_US006153229A_

United States Patent [19]
Foret

[11] Patent Number: 6,153,229
[45] Date of Patent: *Nov. 28, 2000

[54] STABLE GLYCERINE IODINE CONCENTRATE COMPOSITIONS

[75] Inventor: Chris Foret, Shawnee Mission, Kans.

[73] Assignee: West Agro, Inc., Kansas City, Mo.

[*] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 09/163,561

[22] Filed: Sep. 30, 1998

Related U.S. Application Data

[63] Continuation-in-part of application No. 08/831,326, Apr. 2, 1995, Pat. No. 5,885,620.

[51] Int. Cl.⁷ ..................................................... A01N 59/22
[52] U.S. Cl. .......................... 424/669; 424/667; 424/670; 424/671; 514/738
[58] Field of Search ................................. 424/667, 670; 514/738

[56] References Cited

U.S. PATENT DOCUMENTS

| | | |
|---|---|---|
| 1,676,554 | 7/1928 | Hoopman . |
| 1,896,171 | 2/1933 | Harry . |
| 3,028,299 | 4/1962 | Winicov . |
| 3,914,411 | 10/1975 | Askienazy et al. . |
| 4,271,149 | 6/1981 | Winicov et al. . |
| 4,297,232 | 10/1981 | Ruben . |
| 4,839,080 | 6/1989 | Jungermann et al. . |
| 4,985,234 | 1/1991 | Nakamura et al. . |
| 5,368,868 | 11/1994 | Winicov . |
| 5,558,881 | 9/1996 | Corby . |

OTHER PUBLICATIONS

British Pharmaceutical Codex (1923).
Remington's Practice of Pharmacy; Martin and Cook; Mack Publishing Company, 12th Edition (1961).
Godinho et al.; The Interaction of Glycerol and an Iodophor Teat Dip; J. Appl. Bacteriol., 48:449–455 (1980).
Osol et al,; Solubility of Iodine in Glycol–Water solutions; J. Amer.Pharm.Assn.; 41:634 (1952).
Webster's II, pp. 388, 1107, 1984.

*Primary Examiner*—Rebecca Cook
*Attorney, Agent, or Firm*—Hovey, Williams, Timmons & Collins

[57] ABSTRACT

Stable aqueous glycerin iodine concentrates are provided which are adapted for dilution in water to yield germicidal iodine use solutions. The concentrates include from about glycerin, iodine, and iodide ion. Preferably, the concentrates further include one or more additives such as compatible wetting agents, hydrotropes, thickening agents, additional emollients and buffering systems. The quantities of iodide ion and iodine are such that the ratio of iodide ion to iodine is from about 0.5:1 to about 6:1. The concentrates are stable for a period of at least about 3 months at room temperature and are dilutable at a ratio of 1 part concentrate with from about 2–80 parts water. The concentrates can be formulated to give very low free iodine values as concentrates which dramatically increase in diluted use solutions to values which are from about 2 to about 300 times greater than the free iodine in the concentrates.

10 Claims, No Drawings

STABLE GLYCERINE IODINE CONCENTRATE COMPOSITIONS

RELATED APPLICATION

This is a continuation-in-part of application Ser. No. 08/831,326, filed Apr. 2, 1995 now 5,885,620.

BACKGROUND OF THE INVENTION

1. Field of the Invention

The present invention is broadly concerned with aqueous stable glycerin iodine concentrate products which can be diluted with water to form germicidal use solutions. More particularly, the invention pertains to such concentrates which have a high content of glycerin above 30% by weight, iodine, iodide ion and preferably additive(s) (e.g., surfactants, hydrotropes, thickening agents, additional emollients, and/or buffering systems) which upon dilution yield high quality germicidal solutions with elevated free iodine values.

2. Description of the Prior Art

Iodine solutions have been used as germicidal agents for many years. In order to create useful solutions of this type, it is necessary to solubilize the iodine therein. Different solubilization approaches have been used in the past. These include hot processes wherein iodine is reacted with ethylene glycol or nonionic surfactants so that the resulting mixture is soluble in water, and room temperature solubilization using polyoxyethylene nonionic surfactants, polyvinylpyrrolidone or iodide ion. All of these solubilizing agents form a complex with the iodine, which in turn yields solutions (generally referred to as iodophores) which are used without further dilution and have varying concentrations of free or uncomplexed iodine ($I_2$). Free iodine is a critical factor in determining the germicidal effectiveness of such iodine solutions, and therefore control of the free iodine level is very desirable if not essential.

It is known that the stability of aqueous iodine use solutions may depend upon the level of free iodine therein. However, high concentrations of free iodine corresponds to high levels of iodine vapor. In open containers, the iodine vapor will eventually cause a depletion of iodine from the solution. In plastic containers the iodine tends to dissolve into and eventually penetrate the container. Given that use solutions with a high free iodine value are generally more effective germicides, it would therefore be desirable to formulate a product having a low free iodine value during storage but which at the time of use could be adjusted to have a high free iodine value.

Many use solution iodophores designed for topical application are formulated with emollient in order to provide a soothing, skin-protective effect. In addition, most emollients will complex with free iodine thus assisting in adjustment and control of the free iodine content of the iodophore. The most common emollient used in such cases is glycerin, and may be present at a level of from about 1–15% by weight in products such as teat dips. Glycerine iodine use formulations also normally include one or more additives which are necessary to give the final use solutions desired physical properties. For example, surfactants are often used to provide wetting properties to insure complete contact between the surface to be disinfected and the use solution. Hydrotropes are also used to aid in the addition of other ingredients and to insure stability of the use solution. Buffering systems and thickening agents are also sometimes employed.

In recent years, manufacturers have sought to develop germicidal concentrate products which can be diluted with water at the point of use. Concentrates reduce manufacturing and freight costs, save storage space and minimize problem of disposing of containers. While certain types of iodophores can be readily formulated as dilutable concentrates, a significant problem arises when the concentrates contain appreciable amounts of glycerin and attendant additives such as surfactants, hydrotropes, additional emollients, buffering systems and thickeners. Specifically, high glycerin content iodophore concentrates tend to be unstable and rapidly separate into phases. This means that the end user must thoroughly mix the concentrate before dilution thereof. Such a requirement is not only inconvenient for the user, but can lead to use solutions having widely varying free iodine contents owing to inadequate mixing of the separated concentrate. As can be appreciated, if a given use solution has too high a free iodine content, it may be irritating; on the other hand, if the use solution has an inadequate free iodine content, its germicidal properties may be compromised.

To give but one example, a number of surfactants which are quite useful in the formulation of glycerin iodine diluted use solutions are incompatible when employed in the formulation of corresponding concentrates. Thus, polyoxyethylene alcohols, polyoxyethylene nonylphenols, polyalkylene block copolymers and polyvinylpyrrolidone are very difficult to use in concentrate formulations having high glycerin contents.

There is accordingly a need in the art for high glycerin content/low free iodine value iodophore concentrate products which have significant stability over long periods of storage, and which can be readily diluted with water to form use solutions having high, predictable and controlled free iodine contents.

SUMMARY OF THE INVENTION

The present invention overcomes the problems outlined above, and provides greatly improved stable aqueous glycerin iodine concentrates adapted for dilution in water to yield use solutions. The concentrates of the invention are aqueous solutions including from about 0.15–15% by weight iodine, from about 0.15–15% by weight iodide ion derived from an alkali metal iodide or hydriodic acid, and from about 30–87% by weight glycerin, based upon the weight of the concentrate being taken as 100% by weight. The concentrates preferably include one or more additives for giving the final diluted use solutions desired physical properties. Such additives are selected from the group consisting of up to about 10% by weight of a compatible wetting agent, up to about 10% by weight of a compatible hydrotrope, up to about 2% by weight of a compatible thickening agent, up to about 30% by weight of an emollient different from glycerin, a sufficient amount of a buffering system to maintain the pH of the diluted use solutions at a level of from about 3–9, and mixtures of any of the foregoing, with the concentrations of the additives being based upon the weight of the concentrate being taken as 100% by weight. Generally, the concentrates of the invention are dilutable in water at a ratio of one part concentrate with from about 2–80 parts water (1+2 to 1+80 concentrate+water dilutions) to give the use solutions; more preferably, the dilution ratio is 1 part concentrate with from about 3–30 parts water. The iodide ion:iodine ratio of both the concentrates and the diluted use solutions is from about 0.5:1 to about 6:1, preferably from about 0.6:1 to about 3.5:1, and more preferably from about 0.6:1 to about 1.5:1.

As used herein, "free iodine" is the concentration of $I_2$ which is not complexed with other species such as iodide ions $I_3$. A certain concentration of free iodine $I_2$ is always present in iodine solutions because of equilibrium reactions such as

or in general $I_2$ (complexing agent) ⇌ $I_2$+complexing agent. Free iodine is preferably determined by the method of Winicov et al., Proc. Int. Symposium on Povidone, University of Kentucky College of Pharmacy, pp. 186–92 (1983), incorporated by reference herein.

The concentrates of the invention should be stable for a period of at least about three months at room temperature (i.e., about 25° C.) storage, more preferably for a period of at least about six months, and most preferably for a period of at least about one year. As used herein with reference to the concentrates, "stable" means that the concentrates remain as substantially single phase, homogeneous solutions throughout a given storage period at room temperature and at least 90% of the starting iodine concentration remains. "Compatible" concentrate ingredients are those which permit initial mixing of all of the ingredients of the concentrate to form the substantially single phase, homogeneous solutions, and which in combination provide the desirable concentrate stability.

The compatible wetting agents most useful in formulating concentrates of the inventions include sulfonates such as the alkyl sulfonates, aryl sulfonates, alkyl aryl sulfonates, alkyl diphenyloxide disulfonate, dialkyl sodium sulfosuccinates, sulfonated amphoterics such as alkylamphohydroxy propyl sulfonate, polysulfonates such as lignosulfate, $C_8$–$C_{16}$ alkyl polyglycosides, sodium alcohol sulfates, and mixtures thereof. Compatible hydrotropes advantageously include sulfonates such as octane sulfonate, naphthlene sulfonate, and mixtures thereof.

Thickening agents can be selected from the group consisting of cellulose derivatives such as hydroxy ethylcellulose and carboxy methylcellulose, sodium alginate, xantham gum and mixtures thereof. The non-glycerin emollients useful in the invention are generally selected from the group consisting of sorbitol, the alkylene glycols (e.g., ethylene glycol and propylene glycol), the polyols, and mixtures thereof. Buffering systems are generally taken from the group consisting of an acid such as the mono-, di- and tri-$C_2$–$C_{10}$ carboxylic acids (e.g., acetic acid, glycolic acid, oxalic acid and citric acid), inorganic acids such as phosphoric acid, and corresponding salts of the foregoing acids.

$C_2$–$C_{10}$ fatty acids such as lactic acid can also be incorporated into the concentrates of the invention. Generally, these fatty acids form a part of the buffering system. It has been found that low molecular weight fatty acid such as lactic acid can be slowly oxidized by iodine at a concentrate pH above 5, and therefore the most stable concentrates contain no more than about 2% fatty acid at pH>5. If the concentrate pH is 5 or below, the fatty acids are not oxidized as readily, and in such cases as much as 10% fatty acid can be added.

The concentrates hereof may be prepared in a number of ways. The preferred procedure involves combining the water and thickening agents and mixing until a uniform dispersion is obtained. The additional ingredients such as buffering systems, surfactants and hydrotropes are then added and agitated until all ingredients are completely dispersed. Finally, the glycerin, other emollients, iodine and alkali metal iodide are added with agitation to complete the concentrate. Iodine may be added in the form of a complex such as sodium iodide-iodine complex. The formulation process does not require any heat, and therefore the mixing procedure is generally carried out at room temperature. Gentle warming of the mixture or at least 80–100° F. may facilitate preparation of the formulation, but is not required.

A characteristic of the concentrates of the invention is that as concentrates, they exhibit very low free iodine levels. However, upon dilution to form use solutions, the free iodine levels are significantly increased. Upon dilution, the free iodine increases by a ratio of from about 2:1 (free iodine upon dilution:free iodine in the concentrate) to about 300:1, preferably from about 5:1 to about 200:1, and more preferably from about 8:1 to about 150:1. Expressed similarly, the free iodine upon dilution is from about 2 to about 300 times, preferably from about 5 to about 200 times, and more preferably from about 8 to about 150 times, the free iodine in the concentrate. Therefore, the concentrates of the invention exhibit very desirable storage properties without the deleterious effects of high free iodine values. At the same time, upon dilution the end products have the very necessary high free iodine levels for germicidal purposes.

The present invention thus permits preparation of germicidal iodine concentrates having controlled free iodine concentrations, both as concentrates and as use solutions. Accordingly, the concentrates may be formulated to meet the needs of a wide variety of end uses. For example, where a use solution may be exposed to significant amounts of blood, a relatively high concentration of available iodine is necessary because of the tendency of the iodine to react with blood components. On the other hand, where the use solutions are exposed for only a minimal organic load, lower concentrations of available iodine will give proper performance.

Many concentrates of the invention can be formulated with a complete absence of wetting agents and hydrotropes. These concentrates have excellent stability, but their corresponding use dilutions may have relatively poor physical properties because of the lack of the omitted wetting agents and hydrotropes. This is not a serious problem, but it will reduce the germicidal efficiency of the diluted product.

DETAILED DESCRIPTION OF THE PREFERRED EMBODIMENT

The following examples 11–16 describe concentrates and diluted use solutions in accordance with the invention, whereas examples 1–4 describe comparative formulas containing non-ionic surfactants and examples 5–10 demonstrate the properties of several other glycerin-iodide compositions. It is to be understood that these examples are provided by way of illustration only, and nothing therein should be taken as a limitation upon the overall scope of the invention.

EXAMPLE 1

A typical type of 1% iodine, 10% glycerin germicidal use solution was prepared using 10 g of Igepal CO-720 (12 mole nonylphenol ethoxylate), 1.08 g iodine, 0.48 g sodium iodide, 10 g glycerin, 0.5 g citric acid, 0.39 g of 50% sodium hydroxide and sufficient water to give a total weight of 100 g. This mixture goes into solution after about 1 hr. of agitation and is relatively stable.

As a comparison, a concentrate formula was prepared wherein all of the ingredients were tripled. This mixture did not blend properly even after extensive mixing, and the concentrate separated into two layers after sitting overnight. This lack of storage stability is a significant and common problem encountered when attempting to formulate a concentrated germicidal solution containing significant amounts of glycerin.

EXAMPLE 2

In this example, a concentrate was prepared by dissolving 0.1 g Igepal CO-720 (12 mole nonylphenol ethoxylate) in 30 g water. Then 7.6 g of sodium iodide, 5.0 g iodine, 50 g glycerin and sufficient water to give a total weight of 100 g were added to the mixture. After 1 day a precipitate formed in the bottom of the container. As a comparison, the identical formulation was prepared except that the Igepal CO-720 was omitted. This gave a stable concentrate which did not form a precipitate.

EXAMPLE 3

In this example, a concentrate was prepared by dissolving 0.1 g Pluronic P105 (ethylene oxide-propylene oxide copolymer) in 30 g water. Then 7.6 g sodium iodide, 5.0 g iodine, 50 g glycerin and water to give a total weight of 100 g were added. After 1 day, a precipitate formed in the container. A comparative concentration formulation identical to the above was also prepared, except that the Pluronic P105 was omitted. This comparative concentrate was stable and did not yield a precipitate.

EXAMPLE 4

A concentrate was prepared by dissolving 0.1 g Kollidon 30 (PVP) in 30 g of water. Then 7.6 g sodium iodide, 5.0 g iodine, 50 g glycerin and sufficient water to give a total weight of 100 g were added. After 1 day, a precipitate formed. A companion concentrate prepared with these same ingredients, save for the omission of the Kollidon 30, was stable.

Examples 1–4 illustrate that the most common complexing agents used in iodine germicidal solutions create problems where high concentrations of glycerin are used, even when sufficient amounts of iodide are present which would normally tend to maintain the iodine fully solubilized.

EXAMPLE 5

Seventeen g of water were combined with 1.6 g sodium iodide, 1.2 g iodine and 80 g of glycerin. At 20° C., the free iodine content of this concentrate is 2.6 ppm iodine. However, a 1+7 aqueous dilution of the concentrate exhibited a 20° C. free iodine content of 95 ppm.

EXAMPLE 6

48.7 g of water were combined with 7.3 g sodium iodide, 4.0 g iodine and 40 g glycerin. The free iodine content of this concentrate formulation at 20° C. is 2.3 ppm. A 1+3 aqueous dilution of the concentrate exhibited a free iodine value of 74 ppm.

EXAMPLE 7

6.3 g of water were combined with 8.0 g of sodium iodide, 5.7 g iodine and 80 g of glycerin. The free iodine content of this concentrate at 20° C. is 1.4 ppm, whereas a 1+39 dilution had a free iodine value of 148 ppm.

Examples 5–7 illustrate the difference in free iodine level of concentrate solutions versus diluted use forms of the products. The free iodine of the diluted solutions is primarily determined by the ratio of the iodine:iodide concentration. The free iodine of the concentrate is determined mainly by the high concentration of glycerin therein. In comparison, Lugol's solution, which contains 5% iodine, 10% potassium iodide and no glycerin, has a free iodine content of 168 ppm. A 1+7 dilution of Lugol's solution has a free iodine content of 267 ppm. Therefore, for iodine/iodide solutions that are free of glycerin, the free iodine values of the concentrates and of the diluted use solutions are similar.

EXAMPLES 8–10

An iodine concentrate was prepared by combining 16.4 g water, 2.2 g sodium iodide, 0.2 g acetic acid, 1.2 g iodine and 80 g glycerin (Example 8). A similar concentrate was prepared by combining 16.2 g water, 2.2 g sodium iodide, 0.3 g sodium citrate, 0.1 g citric acid, 1.2 g iodine and 80 g glycerin (Example 9). A third concentrate was prepared by combining 16.2 g water, 2.2 g sodium iodide, 0.16 g acetic acid, 0.24 g sodium acetate, 1.2 g iodine and 80 g glycerin (Example 10).

The following table illustrates the stability of the Examples 8–10 concentrates thereof after three weeks storage at 50° C. and dilutions. These formulations show little loss of iodine. The pH of the diluted products is partly dependent on the pH of the water used for the dilution. The storage data demonstrates the stability of the concentrates.

TABLE 1

| Concentrate/Dilution—Property | Example 8 | Example 9 | Example 10 |
| --- | --- | --- | --- |
| 1 + 7 dilution with DI water—pH | 4.1 | 5.2 | 5.0 |
| concentrate at 20° C.—free iodine value | 1.4 ppm | 1.0 ppm | 1.4 ppm |
| 1 + 7 dilution with DI water at 20° C.—free iodine value | 63 ppm | 67 ppm | 68 ppm |
| concentrate—initial percent iodine | 1.17 | 1.15 | 1.17 |
| concentrate—percent iodine after 3 weeks at 50° C. | 1.14 | 1.12 | 1.14 |

EXAMPLE 11

A concentrate was prepared by combining 30 g glycerin, 3 g iodine, 4.6 g sodium iodide, 0.1 g acetic acid, 0.2 g sodium acetate, 0.3 g Glucopon 425 (alkyl polyglycoside), and sufficient water to give a total weight of 100 g. This concentrate can be diluted at 1+5 ratio to give a germicidal use solution containing 0.5% iodine and 5% glycerin.

EXAMPLE 12

A concentrate was prepared by combining 80 g glycerin, 0.57 g iodine, 0.81 g sodium iodide, 0.2 g acetic acid, 0.2 g sodium acetate, 0.35 g Aerosol OT (sodium dioctyl sulfosuccinate), and sufficient water to give a total weight of 100 g. The concentrate can be diluted at a 1+5 ratio to give a germicidal use solution containing 0.09% iodine and 13.3% glycerin.

EXAMPLE 13

A concentrate was prepared by combining 40 gm glycerin, 3.14 gm iodine, 4.57 gm sodium iodide, 1.13 gm of mono basic sodium phosphate monohydrate, 1 gm Mirataine CBS (cocamidopropyl hydroxysultaine), and sufficient water to give a total weight of 100 g. The concentrate can be diluted at 1+19 ratio to give a germicidal use solution containing 0.16% iodine and 2% glycerin.

EXAMPLE 14

A concentrate was prepared by combining 70 g glycerin, 3.5 g iodine, 5.26 g sodium iodide, 0.25 g lactic acid, 0.1 g sodium hydroxide, 0.35 g Aerosol OT (sodium dioctyl sulfosuccinate), 0.35% Keltrol, and sufficient water to give a total weight of 100 g. The concentrate can be diluted at a 1+6 ratio to produce a 0.5% iodine/10% glycerin use solution.

EXAMPLE 15

A concentrate was prepared by combining 40 g glycerin, 4.0 g iodine, 6.06 g sodium iodide, 0.2 g lactic acid, 0.15 g sodium hydroxide, 0.20 g Aerosol OT 75 (sodium dioctylsulfosuccinate), 0.20% Keltrol T (xanthan gum), and sufficient water to give a total weight of 100 g. The concentrate can be diluted at a 1+3 ratio to give a 1% iodine/10% glycerin use solution.

EXAMPLE 16

A concentrate was prepared by combining 50 g glycerin, 1.25 g iodine, 1.88 g sodium iodide, 0.1 g lactic acid, 0.1 g sodium hydroxide, 1.25 Miranol CS (cocoamphohydroxypropylsulfonate), 0.3% sodium alginate, and sufficient water to give a total weight of 100 g. The concentrate can be diluted at a 1+24 ratio to give a 0.05% iodine/2% glycerin use solution.

EXAMPLE 17

A concentrate was prepared by combining 87 g glycerin, 5.7 g iodine, 4.07 g sodium iodide, and 3.23 g water. The resulting concentrate was diluted at a 1+2 ratio to give a 1.9% iodine/29% glycerin use solution. The iodide/iodine ratio of both the concentrate and the use solution was 0.605.

The following Table 2 sets forth approximate broad and preferred ranges for the concentrate ingredients of the invention, which are dispersed in water to make the final concentrates.

TABLE 2

| Concentrate Ingredients[1] | Broad Range | Preferred Range |
| --- | --- | --- |
| Glycerin | 30–87 | 50–80 |
| Iodine | 0.15–15 | 0.6–11.7 |
| Iodide ion from alkali metal iodide or hydriodic acid | 0.15–15 | 0.8–7.3 |
| Wetting Agent | up to 10% | 0.2–4.0 |
| Hydrotrope | up to 10% | 0.2–4.0 |
| Thickening Agent | up to 2% | 0.1–0.5 |
| Emollient different than glycerin | up to 30% | 0–30 |
| Fatty Acid Buffer[2] at pH 5 or above | up to 2% | .2–.5 |
| Fatty Acid Buffer[2] at pH below 5 | up to 10% | .2–4 |
| Inorganic Buffer such as Phosphate | up to 10% | 0.2–4 |
| Dilution Ratio | 1 + 2 to 1 + 80 | 1 + 3 to 1 + 30 |
| pH of Use Dilution | 3–9 | 3–7 |

[1]All data given as percent by weight based upon the weight of the aqueous concentrate taken as 100% by weight, unless otherwise indicated.
[2]pH values refer to pH of concentrate solutions.

I claim:

1. An aqueous stable glycerin iodine concentrate solution consisting essentially of:

from about 0.15–15% by weight iodine;

from about 0.15–15 by weight iodide ion; and from about 30–87% by weight of glycerin, said iodide ion and iodine being present at such a level that the ratio of iodide ion to iodine is from about 0.6:1 to about 6:1, said concentrate being dilutable in water at a dilution ratio of 1 part concentrate with from about 2–80 parts water to yield a use solution having from about 2 to about 300 times the free iodine as said concentrate and wherein said concentrate solution remains as a substantially single phase, homogeneous solution for at least about three months at room temperature and at least 90% of the starting iodine concentration remains.

2. An aqueous stable glycerin iodine concentrate solution comprising:

from about 0.15–15% by weight iodine;

from about 0.8–7.3% by weight iodide ion; and from about 30–87% by weight of glycerin;

said iodide ion and iodine being present at such a level that the ratio of iodide ion to iodine is from about 0.6:1 to about 6:1, said concentration being diluatable in water at a dilution ratio of 1 part concentrate with from about 2–80 parts water to yield a use solution having from about 2 to about 300 times the free iodine as said concentrate and wherein said concentrate solution remains as a substantially single phase, homogeneous solution for at least about three months at room temperature and at least 90% of the starting iodine concentration remains.

3. The concentration of claim 2, said use solution having from about 5 to about 200 times the free iodine as said concentrate.

4. The concentration of claim 3, said use solution having from about 8 to about 150 times the free iodine as said concentrate.

5. The concentration of claim 2, said concentrate further including an additive selected from the group consisting of wetting agents, hydrotropes, thickening agents, emollients different from glycerin and buffering systems to maintain the pH of said use solutions at a level of from about 3–9, or a mixture thereof.

6. An aqueous stable glycerin iodine concentrate solution comprising:

from about 0.15–15% by weight iodine;

from about 0.87–7.3% by weight iodide ion; and from about 30–87% by weight of glycerin, said concentrate being dilutable in water at a dilution ratio of 1 part concentrate with from about 2–80 parts water to yield a use solution, said iodide ion and iodine being present at such a level that the ratio of iodide ion to iodine is from about 0.6:1 to about 6:1, and wherein said solution remains as a substantially single phase, homogeneous solution for at least about three months at room temperature and at least 90% of the starting iodine concentration remains.

7. The concentrate of claim 6, said iodide ion to iodine ratio being from about 0.6:1 to about 3.5:1.

8. The concentrate of claim 7, said iodide ion to iodine ratio being from about 0.6:1 to about 1.5:1.

9. The concentrate of claim 6, said concentrate further including an additive selected from the group consisting of wetting agents, hydrotropes, thickening agents, emollients different from glycerin and buffering systems to maintain the pH of said use solutions at a level of from about 3–9, or a mixture thereof.

10. The concentration of claim 6, said use solution having from about 2 to about 300 times free iodine as said concentrate.

* * * * *

UNITED STATES PATENT AND TRADEMARK OFFICE
CERTIFICATE OF CORRECTION

PATENT NO. : 6,153,229
DATED : November 28, 2000
INVENTOR(S) : Chris Foret

It is certified that error appears in the above-identified patent and that said Letters Patent is hereby corrected as shown below:

Title Page,
Item [63], delete "1995" and substitute therefore -- 1997 --.

Column 1,
Line 6, delete "1995" and substitute therefore -- 1997 --.

Signed and Sealed this

Thirtieth Day of October, 2001

Attest:

*Nicholas P. Godici*

NICHOLAS P. GODICI
*Attesting Officer*     *Acting Director of the United States Patent and Trademark Office*